United States Patent [19]
Busch et al.

[11] Patent Number: 5,208,458
[45] Date of Patent: May 4, 1993

[54] INTERFACE DEVICE TO COUPLE GEL ELECTROPHORESIS WITH MASS SPECTROMETRY USING SAMPLE DISRUPTION

[75] Inventors: Kenneth L. Busch, Marietta, Ga.; Stephen M. Brown, Jr., St. Johns, Mich.

[73] Assignee: Georgia Tech Research Corporation, Atlanta, Ga.

[21] Appl. No.: 788,311

[22] Filed: Nov. 5, 1991

[51] Int. Cl.[5] .................... B01D 59/44; H01J 49/00
[52] U.S. Cl. .................................. 250/288; 250/281; 250/282
[58] Field of Search ............ 250/281, 282, 288, 423 P

[56] References Cited
U.S. PATENT DOCUMENTS

| | | |
|---|---|---|
| 4,046,012 | 9/1977 | Studenick .................. 250/288 |
| 4,620,103 | 10/1986 | Kambara et al. ........... 250/288 |
| 4,705,616 | 11/1987 | Andresen et al. .......... 250/288 |
| 4,708,782 | 11/1987 | Andresen et al. .......... 250/288 A |
| 4,814,612 | 3/1989 | Vestal et al. ................ 250/282 |
| 4,842,701 | 6/1989 | Smith et al. ................ 250/288 |
| 4,920,264 | 4/1990 | Becker ........................ 250/288 |

Primary Examiner—Bruce C. Anderson
Attorney, Agent, or Firm—Deveau, Colton & Marquis

[57] ABSTRACT

An interface for the direct introduction of a sample taken from a planar electrophoresis into a mass spectrometer or other spectrometric device. The interface comprises a probe to collect a sample from a planar electrophoresis, generally a gel electrophoresis, and a filter and guard column configuration to remove unwanted and unnecessary impurities and excess solvent, and to concentrate the sample prior to introduction to the mass spectrometer.

27 Claims, 9 Drawing Sheets

INTERFACE DEVICE TO COUPLE GEL ELECTROPHORESIS WITH MASS SPECTROMETRY USING SAMPLE DISRUPTION

BACKGROUND OF THE INVENTION

1. Field of the Invention

This invention relates generally to the field of introducing samples to a mass spectrometer and more specifically to an interface for introducing samples obtained from disrupted gel electropherograms to mass spectrometry devices for analysis.

2. Prior Art

Mass spectrometry is the most specific detection method available for coupling to chromatographic separation methods, and provides a high level of sensitivity for most compounds. Coupling of mass spectrometry to gas chromatography and liquid chromatography is well known. Supercritical fluid chromatography and capillary zone electrophoresis (CZE) have also been coupled to mass spectrometers.

Devices for the direct analysis of liquid streams by mass spectrometry have been increasingly evident in recent literature. In particular, the development of continuous flow fast atom bombardment (FAB) mass spectrometry has been an area of vigorous research. Analytical advantages of the flow FAB probe include lower chemical background noise (compared to conventional FAB probes), reduced ion suppression effects for mixtures of samples with varying surface activities, and generally lower detection limits. Practical advantages include the fact that introducing samples via a flow stream greatly simplifies and quickens FAB measurements even for discrete samples. Continuous-flow fast atom bombardment interfaces for liquid chromatography have been widely adopted.

Several references in the literature describe the coupling of capillary zone electrophoresis (CZE) with mass spectrometry. This is a fundamentally different form of separation and is not considered relevant to the present invention. Two recent papers describe an indirect coupling based on separate extraction of samples from gel electropherograms and off-line analysis by fast atom bombardment mass spectrometry (FABMS): P. Camilleri et al., 3 Rap. Comm. Mass Spec., 346 (1989); 440 (1989). Camilleri et al. reported the extraction of samples from polyacrylamide gels, with subsequent analysis of the discrete samples by FABMS. However, the necessary sample preparation included an extended extraction of the gel with strongly acidic solvents and crushing of the gels after sample bands were excised from the gel.

Similarly, Duffin et al. (as reported in an abstract at a recent meeting) have extracted biological samples from within gels with the aid of an extended sonication time and a series of eluting solvents, and have shown that FAB analysis provides good quality mass spectra of these extracts. Duffin's extraction apparently involved a slice of gel of about 0.5 cc in volume placed in a test tube of extraction solvent. The gel and solvent were sonicated overnight and then evaporated to near dryness. The residue was taken up in a FAB solvent and the analysis of the residue was performed as if the sample was a discrete sample generated by any other means. Duffin's process is a standard recovery procedure known to those skilled in the art and samples recovered from procedures similar to Duffin's also are used in unrelated art. The data of Duffin show, and it is generally agreed that relatively drastic means are required to release large biological samples from gel matrices in which they are encapsulated. Even high power laser desorption can be insufficient for extraction, although our own recent results suggest that conditions can be found that release intact molecular ions of nucleotides from dried agarose gels.

Previous mentions of planar chromatography coupled with mass spectrometry are our own, but none of these relate specifically to the present invention. (K. L. Busch, 6 Trends Anal. Chem., 95 (1987); M. S. Stanley et al., 200 Anal. Chem. Acta, 447 (1987); M. S. Stanley and K. L. Busch, 1 J. Planar Chrom. 135 (1988). Our previous work in coupling planar chromatography with mass spectrometry relate to combinations of mass spectrometry with high performance thin-layer chromatography, or to applications of electrophoresis with mass spectrometry that involve transfer of the samples to a secondary substrate. In this former work, there is no separate interface necessary because the primary particle beam sputters material from the gel surface directly. A Phase-transition matrix sometimes is involved in the former work, but there is no transfer of material out of the chromatographic medium through capillary transfer lines to the source of the mass spectrometer as the entire chromatogram is placed within the vacuum chamber of the mass spectrometer. The present invention, when compared to the former work, had several distinguishing factors, including the Present invention's ability to extract the sample material directly from a PAGE (polyacrylamide gel eletrophoresis, agarose, or other gel with a variety of solvents; concentration of the sample; removal of extraneous components in the system; and the transfer of the sample in a flow stream of solvent through a capillary line to the source of the mass spectrometer.

The methods used for recovering material from gel electropherograms depend mainly on the subsequent steps to be performed on the recovered analyte, such as sequencing or situ reactions (immunoassay). The general problem of recovering DNA/RNA or proteins from gels lies in the physical barriers that the large molecules encounter. That is, the long strands of biopolymer are so well enmeshed inside the gel that the molecules have to be coaxed rather strongly to be released. The gel itself generally is immune to the types of chemical attack that are sufficient to destroy the biopolymer itself.

The need to recover materials from gels is ongoing. The most widely used separation method by the biological community is planar electrophoresis, with an extensive tradition and repertoire built over years of experience with the method applied to provide high resolution, multi-dimensional separations of complex biological mixtures. PAGE (polyacrylamide gel electrophoresis) and agarose gel electrophoresis are high capacity, high precision, and high dynamic range methods. Bioanalytical protocols are based explicitly on these methods, and have been optimized over twenty years of continuous use. New developments in CZE and its variants will complement, but certainly will not supplant, the methods of planar electrophoresis. Although many detection methods have been developed in conjunction with planar electrophoresis, to date no process or method has coupled mass spectrometry with that separation method.

Most proteins are separated by polyacrylamide gel electrophoresis (PAGE) (based on the molecular weight) or modified polyacrylamide gel isoelectric focusing (based on molecular charge). Both of the techniques can be used in tandem in a two-dimensional approach for maximum resolution. Polyacrylamide gels are made by polymerizing the monomer, acrylamide, into long strands, and then linking the strands together with a 'cross-linker', usually N,N'-methylene-bisacrylamide (Bis). The relative proportions of these components will determine the separation characteristics of the gel. Isoelectric focusing is carried out in a PAGE gel that contains an immobilized pH gradient consisting of high molecular weight polyaminocarboxylic acids (ampholytes).

Other known methods for separating a desired material from a gel include direct extraction, electroblotting, electroelution, capillary blotting, sonication, and electrophoresis.

The direct extraction method involves cutting out the band of interest from the gel, mashing it and immersing it in a buffer solution of Tris ((tris-hydroxymethyl)-aminomethane), glycine and SDS. The mixture is shaken, after which it is filtered and the protein recovered by extraction. This method is highly unsatisfactory for large proteins (extremely low recovery) even under these extreme conditions due to the fact that diffusion of large proteins from within the complex gel network is an inefficient process.

Direct extraction methods also can be used for small nucleic acid strands. Agarose gels can be dissolved in 6M $NaClO_4$; the solution is then filtered, extracted with appropriate solvents and the DNA is precipitated. Nucleic acids separated by PAGE gels can be extracted directly in a manner similar to that for proteins by mashing the gel, putting it into a medium of high ionic strength, such as ammonium acetate, which promotes diffusion of DNA out of the gel, SDS, and a magnesium salt to aid precipitation of DNA. Sample molecules dissolved in the aqueous gel extract are then precipitated with ethanol.

Electroblotting, the most common and satisfactory method of recovering proteins, involves transfer of the proteins from the gel onto another equally sized membrane, using an electric current to drive their migration in a manner similar to the original electrophoresis (Western blot), but in a perpendicular direction. Although there are many variations on this technique, it essentially involves making a sandwich of the gel and the transfer membrane (commonly nitrocellulose) between two layers of filter paper. This sandwich is then placed into a tank of transfer buffer solution and a low current is passed through the tank across the sandwich. The reason for performing an electroblot is that the proteins are now more accessible on the transfer membrane than they were in the gel. For instance, detection techniques are more sensitive and the proteins on the membrane can be reacted in situ, with antibodies or other agents.

One commonly used method of recovering a sample by electroelution uses a dialysis bag. The portion of gel containing the nucleic acid of interest is cut out and put into a dialysis bag filled with buffer. After the gel has sunk to the bottom of the bag, the excess buffer can be removed. The bag is then immersed in a shallow tank of buffer and electric current is passed through the bag. The nucleic acid is then electroeluted onto the wall of the bag. The polarity of the current is reversed for a short time to release the nucleic acid from the wall of the bag. The nucleic acid is thereby recovered and purified. A second commonly used method of electroelution is trough electroelution, which involves cutting a trough in the gel on the leading edge of the selected band. The trough is filled with buffer and electrophoresis continues, with the nucleic acid being moved into the trough. The buffer in the trough is withdrawn and replaced a few times until all of the nucleic acid is recovered in solution. A more ingenious method involves putting a dialysis membrane vertically in the trough and electroeluting the nucleic acid from the gel onto the membrane.

Nucleic Acids (DNA/RNA) and their components commonly are separated by agarose gel electrophoresis, although PAGE often is used to separate complementary strands of denatured DNA/RNA.

Capillary blotting of DNA/RNA was developed first by Southern (Southern blot); the geographical pun is continued in the derived name of a Western Blot. In a Western blot, the blotting proceeds by capillary pressure. It should be noted that the Southern blot also works well for peptides and small proteins from PAGE gels.

In order to make biomolecule recovery easier, the structure of the gels used in electrophoresis may be changed, thus changing their chemical or physical properties. PAGE gels can be modified by using cross linkers alternative to bisacrylamide. Alternative cross-linkers include N,N'-(1,2 dihydroxyethylene) bisacrylamide (DHEBA), ethylene diacrylate (EDA), and N,N'-bisacrylcystamine (BAC). Once the cross-linking is disrupted, the gel can be solubilized and the biomolecules can more readily diffuse out. As with any of the methods described above, the time required, the recovery, and the capability for repetitive application to the many bands separated on a gel are, in general, unsatisfactory.

In sonication extraction of samples from electrophoretic gels, a small piece of the gel is excised from the larger gel, mixed with solvent in a tube or small flask, and then sonicated in a standard ultrasonic bath for some period of time, usually hours, but sometimes overnight. The sonication increases the rate of diffusion of the sample molecules from within the pores of the electrophoretic gel out into the solvent added to the sample. The sonication does not by itself usually disrupt the cross-link structure of the gel. Extended sonication can, however, result in degredation of the sample molecules themselves.

Extraordinary resolution in separation is available with CZE, but it is still a relatively new technique, and is used for compounds of relatively low mass in comparison with the masses of those separated by gel electrophoresis. Various forms of gel (agarose or polyacrylamide) electrophoresis are utilized in virtually every biochemical laboratory for samples of molecular weights of several thousand to several hundred thousand daltons. The coupling of mass spectrometry with these gel electrophoretic techniques would benefit a great number of researchers searching for a more selective and information-rich detection method.

BRIEF SUMMARY OF THE INVENTION

The apparatus of the present invention is used as an interface device between various forms of planar electrophoresis, including slab gel electrophoresis, and mass spectrometry. The device consists of a means of delivering a supply of solvent at a specified rate to the surface of the electropherogram, a system to disrupt the gel and release the sample molecules contained therein so that they can be taken up into the solvent, a system to concentrate the sample and separate molecules of interest from developing solvent components, buffers, and modifiers as well as gel fragments, and a transfer line to transmit the volume of solvent containing the extracted sample to the source of a mass spectrometer. Sample bands on a gel are extracted and material transferred to the mass spectrometer ion source, which can operate with any of several different and complementary ionization methods. Mass spectrometric information is correlated with the (x, y) location of sample bands in the electropherogram.

The interface device places no intrinsic limits on the operation of the ionization source of the mass spectrometer. A second advantage of this interface device is its real-time operation. Mass spectra are produced for each sample band in the order examined, and for as long as that sample band remains under investigation.

Another advantage of this interface device is its adaptability to different solvent systems and size requirements. Solvent composition can be varied as necessary to release sample molecules from the gel, and the dimensions of the interface are consistent with the size of bands usually encountered in gel electrophoresis. (a few square millimeters)

Yet another advantage of this interface is its ability to couple the system with a nondestructive means of sample band location. Usual means of sample band location such as optical densitometry are of course non-destructive, and are compatible with the mass spectrometric interface. Simultaneous use of optical densitometry with mass spectrometric detection is possible. All sizes of planar chromatograms can be studied with the interface device.

The interface apparatus has provided positive results on biological materials including a small enzyme, peptides, and other model compounds such as angiotensin and nucleic acids.

For the first time, this invention provides the means to interface gel electrophoresis (planar electrophoresis in general) with mass spectrometry. The majority of users of electrophoresis use gel (planar) electrophoresis rather than capillary zone electrophoresis.

With this new interface device, we use a localized mechanical disruption of the gel coupled with in situ solvent extraction to release biological materials from the matrix. Solvents are supplied in a continuous stream to the site of disruption, and eluent is transferred through a flow capillary into the ion source of the mass spectrometer.

These and other advantages, features and objects will become apparent to one skilled in the art when the following detailed description of a preferred embodiment is read in conjunction with the following figures in which like components are designated by corresponding numerals throughout the several views.

DETAILED DESCRIPTION OF A PREFERRED EMBODIMENT

1. The System

The specification describes a system comprising an external homogenization probe coupled with continuous flow fast atom bombardment (FAB) ionization into a mass spectrometer. This system uses a rotor/stator homogenization probe that is lowered onto the surface of the aqueous gel, and releases the sample molecules into a flow stream that is processed and then sent to the source of the mass spectrometer. The key to the successful coupling of mass spectrometry to planar gel electrophoresis is the rapid homogenization of the gel and release of the sample molecules into a flow stream. In the rotor/stator homogenizer, this release of the sample into the flow stream generally occurs in about 30 s. With this speed, discrete areas of the planar electropherogram can be selected for analysis on a convenient time scale.

This invention is used as an interface device between various forms of electrophoresis, including gel electrophoresis, and mass spectrometry. The device consists of a means of delivering a supply of solvent at a specified rate to the surface of the electropherogram, a system to disrupt the gel and release the sample molecules contained therein so that they can be taken up into the solvent, and a transfer capillary line to transfer the volume of solvent containing the extracted sample to the source of a mass spectrometer.

There are no intrinsic limits on the operation of the mass spectrometer, including the ionization method selected, polarity of ions analyzed, or resolution of operation. There are no limits on the operation of the transfer capillary but that the gas or liquid load into the source of the mass spectrometer be consistent with the vacuum requirements of the mass spectrometer source. There are no limits on the operation of the disruption system save that the volume disrupted be consistent with the size of the bands separated within the electropherogram, and that the solvent flow admitted to the surface is a function of the volume disrupted. There is no limitation which requires that the surface disruption be performed by a rotor/stator homogenizer, as any one of a number of proven disruption systems could be adapted for use in the device (such as a piezoelectric transducer-based homogenizer). There are no limits on the solvent composition other than the requirement that it serve to dissolve the sample of interest without causing degradation, and be consistent with the operation of the mass spectrometer ionization method.

By way of example, a system interfaced to a continuous flow FAB probe ordinarily would operate with a solvent that contains some percentage of the FAB matrix so that the experiment could be completed in the normal manner. Key advantages to the interface device are the real-time operation, the adaptability to different solvent systems as used in flow FAB and size requirements since the disruption occurs outside of the vacuum of the mass spectrometer, and the ability to couple the system with an independent, nondestructive means of sample band location such as the optical densitometry systems already in widespread use.

Variations and alternative embodiments of the invention include mechanical disruption of electropherogram, ultrasonic disruption of electropherogram, laser-beam disruption of electropherogram, and the use of low-melting-point or dissolvable gels alone with solvent extraction or in combination with any of the above. Low melting point gels are defined as gels which melt at temperatures below the temperatures that might degrade the samples originally separated by the electrophoresis. Normally, these gels melt in the range of approximately 30°-40° C. Soluble gels generally are defined as gels with cleavable cross-linkers. The cross-link is the bond that sets-up the gel from the original casting solution. If the cross-linking bond is something like a disulfide bond, the addition of dithiothreitol to the solvent mixture reproducably breaks the bond and aids chemically in the disruption of the gel and the release of the sample molecules into the solvent stream. Further alternative embodiments include a mass spectrometer which uses flow FAB ionization or LSIMS, electrospray operation, or any other ionization method, such as electron or chemical ionization, laser desorption, or plasma desorption.

The present system incorporates a number of unique features, including:

1) use of a more rapid Piezoelectric homogenizer;
2) convenient dispersal of gel slurry in a larger solvent volume;
3) concentration of sample in a smaller flow volume for final transfer;
4) removal of surfactants, buffers, and salts;
5) compatibility with alternative detection schemes; and
6) compatibility with ionization methods for high mass biomolecules such as those separated by electrophoresis.

a. The Apparatus

Figure 1:
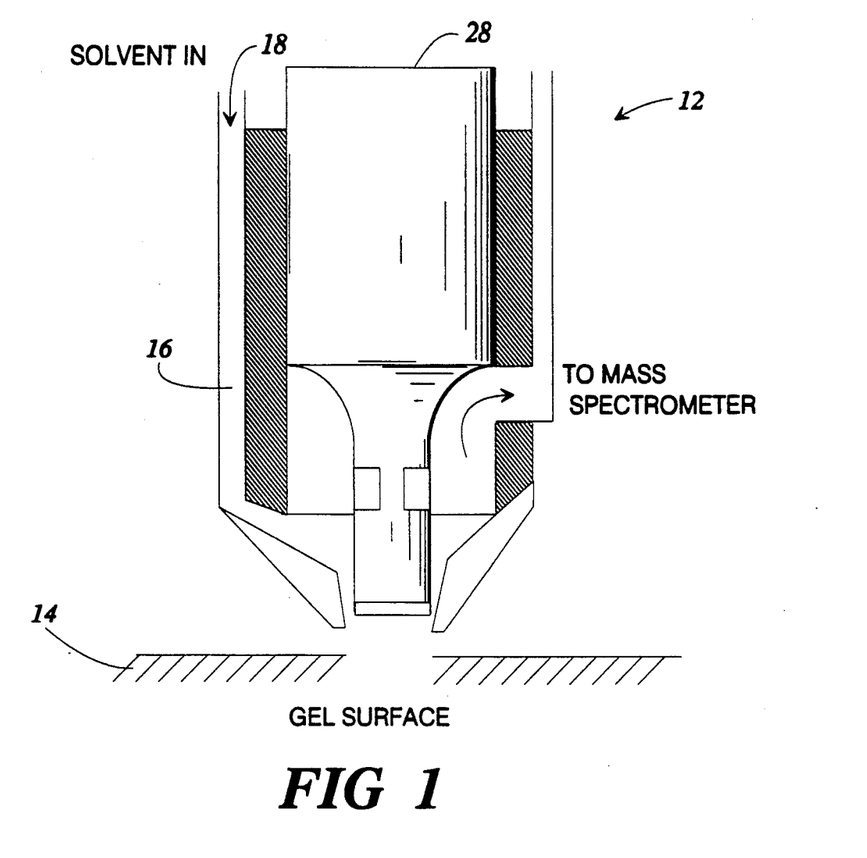
FIG. 1 is a side elevational view, partly in section, of one embodiment of the probe used to obtain sample in the present invention.
Figure 2A:
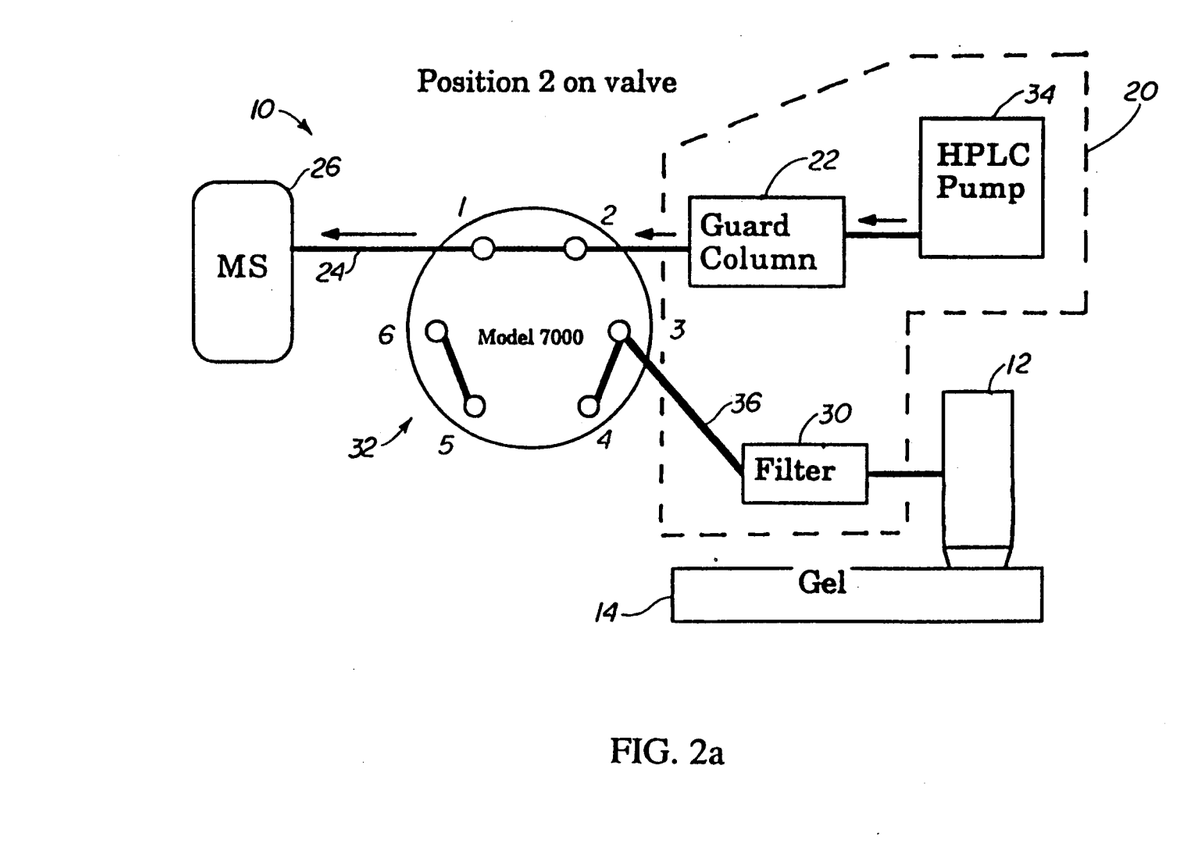
FIG. 2a is a block diagram of the apparatus of the present invention shown in the sample extraction mode.
Figure 2B:
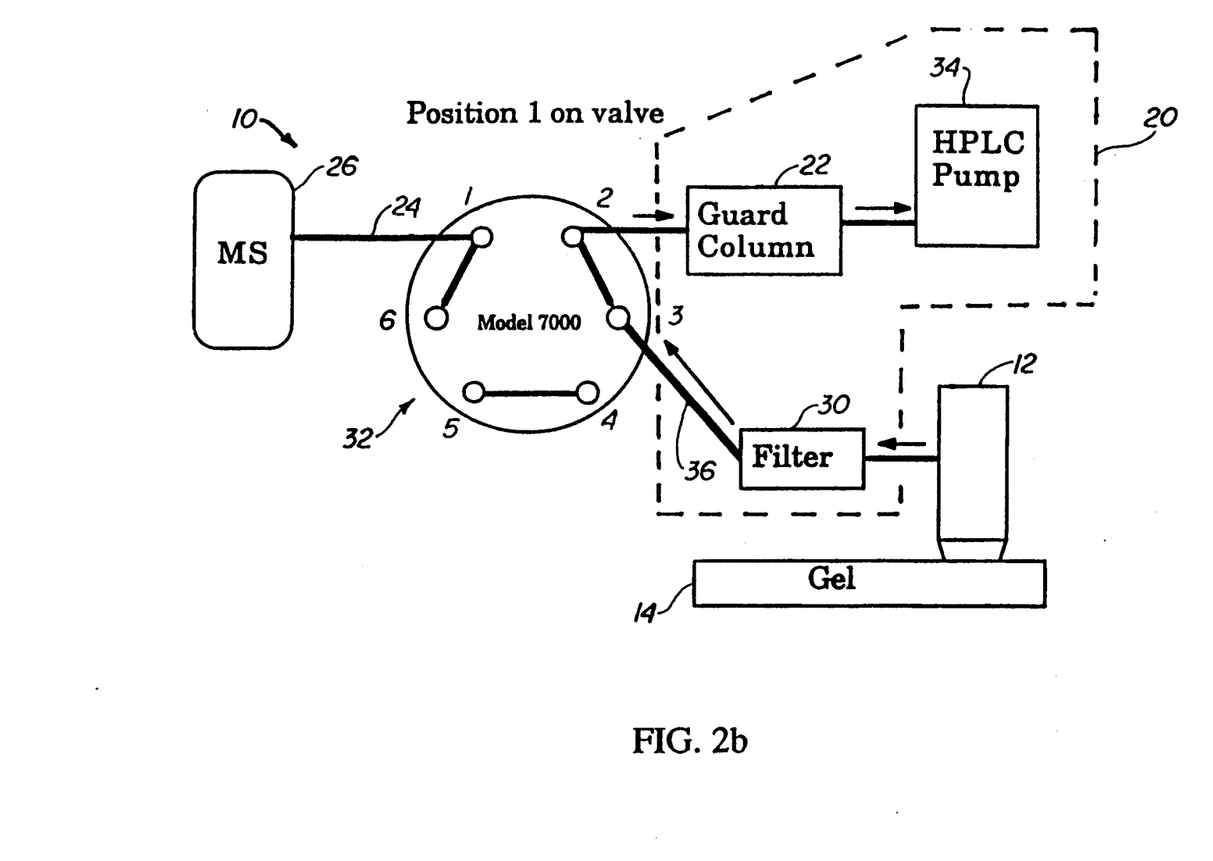
FIG. 2b is a block diagram of the apparatus of the present invention shown in the sample introduction mode.
Figure 3:
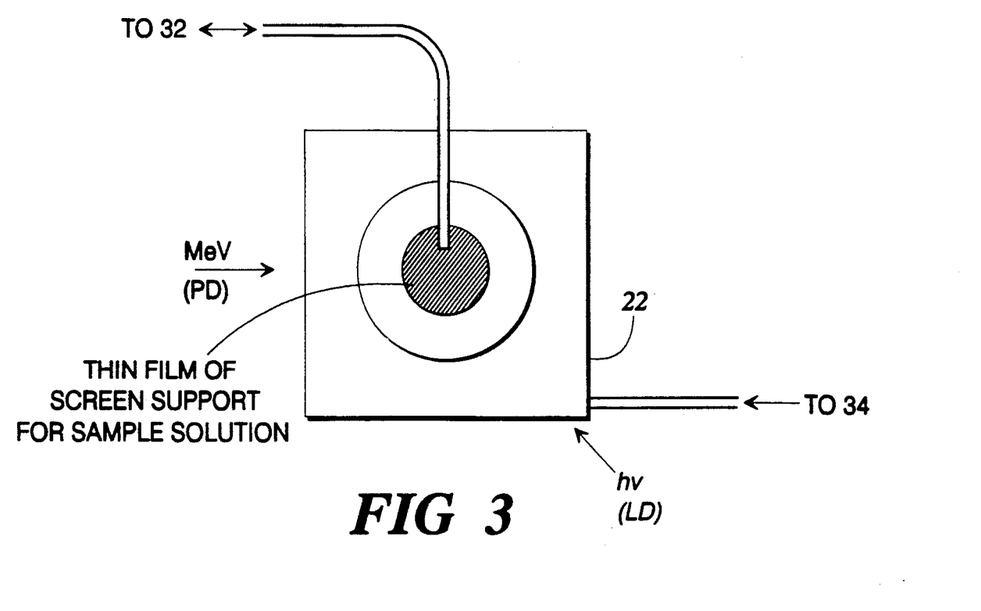
FIG. 3 is a block diagram of the filter/concentrate apparatus of the present invention.

With reference to FIGS. 1-3, sample bands are located on the electrophoretic gel 14. The desired band is physically isolated, and a suitable solvent 18 added to the isolation sleeve 16 of the probe 12. The probe 12 is lowered to homogenize the sample, thereby disrupting the gel 14 and releasing the sample into the solvent 18. The solvent 18 is drawn from the isolation sleeve 16 into a concentration column 20. Aqueous solvents and salts are drawn completely through the column to waste; the sample molecules are retained by adsorption on the front of the guard column 22. After all solvent has been processed, the flow through the column is reversed with solvent composition now chosen for continuous flow FAB analysis or electrospray ionization. The solvent flow is led through a transfer capillary 24 to the source of the mass spectrometer 26. The solvent flow diagram is shown in FIG. 2.

The apparatus of the present device utilizes mechanical homogenization of localized bands in the gel 14. A probe 12 comprising either a rotor/stator homogenizer, a piezoelectric transducer, or an ultrasonic generator is generally best-suited for the mechanical homogenization, although other equivalent devices may be used. The probe 12, upon the addition of appropriate solvent 18 to the gel 14, creates a slurry of gel microparticles dispersed in the solvent. This slurry is then passed through a screen filter 30 to remove the gel particles. Screen filter 30 is located between probe 12 and valve 32 and, besides removing any gel 14 particles not small enough for proper later analysis, removes particulate impurities from the gel slurry. The filtered gel slurry then is pulled into the pre-concentration column 22 via action of a high pressure pump 34 before going onto the source of the mass spectrometer.

In pre-concentration column 22, the gel slurry is concentrated to generate a gel sample of sufficient quantity for proper analysis in the mass spectrometer 26. Column 22 comprises a column filter system (not shown), such as that in a high pressure liquid chromatograph that allows the collection of the gel sample on the column filter. Solvent 18 and other fluids are pulled through the column filter by the high pressure pump 34, such as a vacuum HPLC pump or other pump, and either exhausted, recycled or saved for future use. When a gel sample of sufficient quantity has been generated on the column filter, the flow profile from the high pressure pump 34 is reversed and the gel sample is forced from the column filter and through transfer capillary 24 to the mass spectrometer 26. A second solvent, selected for compatability with continuous flow FAB analysis or electrospray ionization, is used to carry the gel sample off of the column filter, through the transfer capillary 24 and into the mass spectrometer 26.

A two-position valve 32 is located between the gel 14/probe 12/filter 30 grouping, the pre-concentration column 22/pump 34 grouping, and the mass spectrometer 26. As shown in FIG. 2a, the valve 32 in its first position allows the gel 14/probe 12/filter 30 grouping to be in fluid communication with the pre-concentration column 22/pump 34 grouping. As shown in FIG. 2b, the valve 32 in its second position allows the pre-concentration column 22/pump 34 grouping to be in fluid communication with the mass spectrometer 26.

In operation, when solvent 18 is being introduced to the gel 14 via probe 12, valve 32 is in its first position, allowing pump 34 to pull the gel slurry from the gel 14 surface, through filter 30, through valve 32 and into pre-concentration column 22. After a gel sample of sufficient quantity has been collected on the column filter, valve 32 is switched to its second position, and the flow of the pump 34 is reversed. A continuous flow FAB analysis or electrospray ionization compatible solvent is now introduced to the pre-concentration column 22 to carry the solution from the gel sample to the mass spectrometer 16. Pump 34 then forces the solvent through the column filter where the gel sample is released into the solvent. The gel sample containing solvent is then forced through valve 32 and transfer capillary 24 into mass spectrometer 26 for analysis.

The schematic of a probe 12 design for more efficient and localized disruption of the gel matrix 14 which effectively releases analyte into an applied solvent is shown in FIG. 1. In this setup, disruption of the surface 14 occurs with the use of a micro-homogenizer 28 (rotor/stator or piezoelectric). Solvent 16 is brought to the surface with a supply capillary at a rate preferably of about 5 microliters per minute, and then passed out of probe 12 through an online filter 30 into the transfer line 36 and through the valve 32 and concentrator column 22, as described above, and then to a flow-FAB or electrospray ion source. The supply flow of solvent is regulated by a syringe pump (not shown). Transfer line flow is regulated by the pressure difference into the vacuum of the mass spectrometer 26.

The homogenizer 28 is mounted on a precision vertical travel rail. The gel 14 is mounted in a fixed position on an x-y manipulation stage, outside the mass spectrometer 26 on a separate stand. In this way, individual bands of material separated within the gel can be selected for mass spectrometric analysis by x-y movement.

The attractiveness of this approach is its versatility. The transfer capillary 24 can be interfaced to a variety of ionization techniques, including a flow-FAB probe, an electrospray source, or other ionization methods, backed by a sector, time-of-flight, FTILR, or a quadrupole ion trap. Also, because the extraction takes place at atmospheric pressure, many different solvents can be introduced locally onto the gel through the solvent inlet capillary, as needed to extract the sample, as long as glycerol or other FAB matrix is added as necessary when the solution is passed to the flow FAB probe.

Since this device represents a simple interface between planar electrophoresis and mass spectrometry, no special limits on the operation of the mass spectrometer are imposed. While the specific applications shown in the Figs. involve the use of continuous flow fast atom bombardment mass spectrometry to demonstrate the operation of the interface, coupling of the transfer capillary to an electrospray ionization source also is straightforward. Particular advantages of the electrospray ionization source are its ability to deal with sample molecules directly in a liquid solvent flowing into the mass spectrometer, and the ability to create multiply-charged ions so that even biomolecules of very high mass are accommodated within a mass range of a few thousand daltons for the mass analyzer. This Specification includes the coupling of this interface device to an electrospray ion source.

b. Variations of the System

In alternate embodiments, the interface device of the present invention may be coupled with electron and chemical ionization, laser desorption and plasma desorption mass spectrometry, and electrospray ionization in all of their forms as ionization methods. As a specific example in the latter instances, the flow from the transfer capillary 24 can be terminated in a wick or thin membrane material of the same support materials already used as sample supports in laser desorption and plasma desorption mass spectrometry. The sample is distributed over the surface either as a spray, as a flowing film, or by capillary action through a thin layer of the substrate. The desorption and ionization then takes place as before. In particular, the demonstrated capabilities of laser desorption and plasma desorption ionization in concert with time-of-flight mass analysis include the determination of molecular weights of biomolecules of the size usually separated by electrophoresis, and the use of this interface as a carrier of such molecules from the gel to the source of the mass spectrometer operated in such a manner is included within this disclosure.

c. Example Of System Operation

Standard solutions of Coenzyme $B_{12}$ (2 mg/mL) and angiotensin II (0.8 mg/ml) were made in water. A small piece of agarose gel, approximately 0.5 cm square, was placed into each standard solution and allowed to stand at room temperature for 18 hours. This ensured uniform diffusion of the analyte into the gel matrix. The pieces of gel containing the analyte were then removed from solution, washed with distilled water to remove any residual analyte from the surface of the gel, and placed in a sample vial. Approximately 1 mL of $H_2O$ was added to each vial. The gel was then homogenized completely with a rotor/stator type micro-homogenizer for a period of 60 s for the entire gel volume. The piezoelectric homogenizer also could be used.

In each case, the smallest diameter tips available commercially were used; a volume of approximately 100 microliters could be homogenized. Simple modifications to decrease the homogenized volumes are elusive with the rotor/stator device since there are limits on the sizes of the mechanical parts. Piezoelectric homogenizers require redesign of the transducer horn to minimize the disruption volume. Piezoelectric homogenization provides a more rapid and complete homogenization due to increased cavitation within the gel. The resulting slurry from the gel is passed through a 5 micron syringe filter to remove any particulate gel matter. Glycerol was added to the filtrant to yield a 10% glycerol concentration. The sample was introduced into the mass spectrometer by immersing the flow-FAB probe capillary into these solutions. The entire sample preparation operation (homogenization, filtration, matrix addition and transfer) took less than 5 minutes to complete even under manual control.

Continuous-flow FAB analysis was performed on a VG-70 SE mass spectrometer. The standard VG dynamic FAB probe was used, with a 50 micron ID, 500 micron OD capillary. The source block of the instrument was heated to 40° C. To enhance the sensitivity of the analysis, the extracted samples were determined using the MCA mode (with magnet scanning) of the mass spectrometer. No background subtraction of the spectra was performed. Spectra were taken once a stable ion signal was obtained, approximately one minute after the transfer capillary was introduced into the sample solution.

Figure 3A:
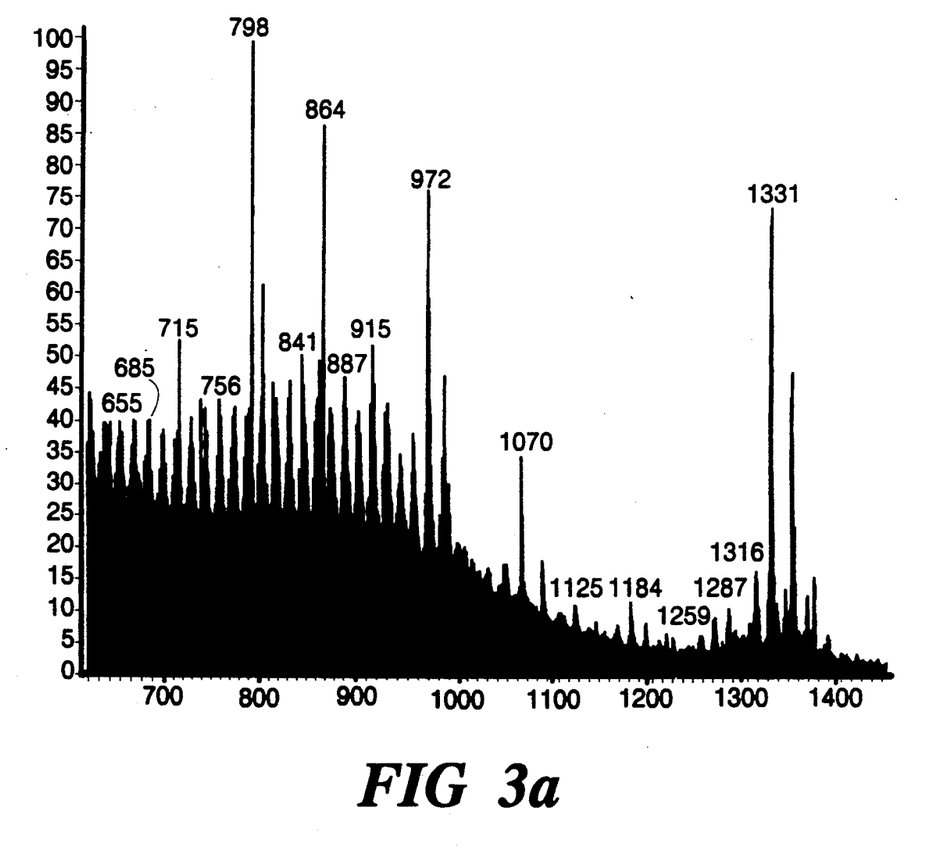
FIG. 3a is the positive ion flow-FAB mass spectrum of coenzyme $B_{12}$ standard.
Figure 3B:
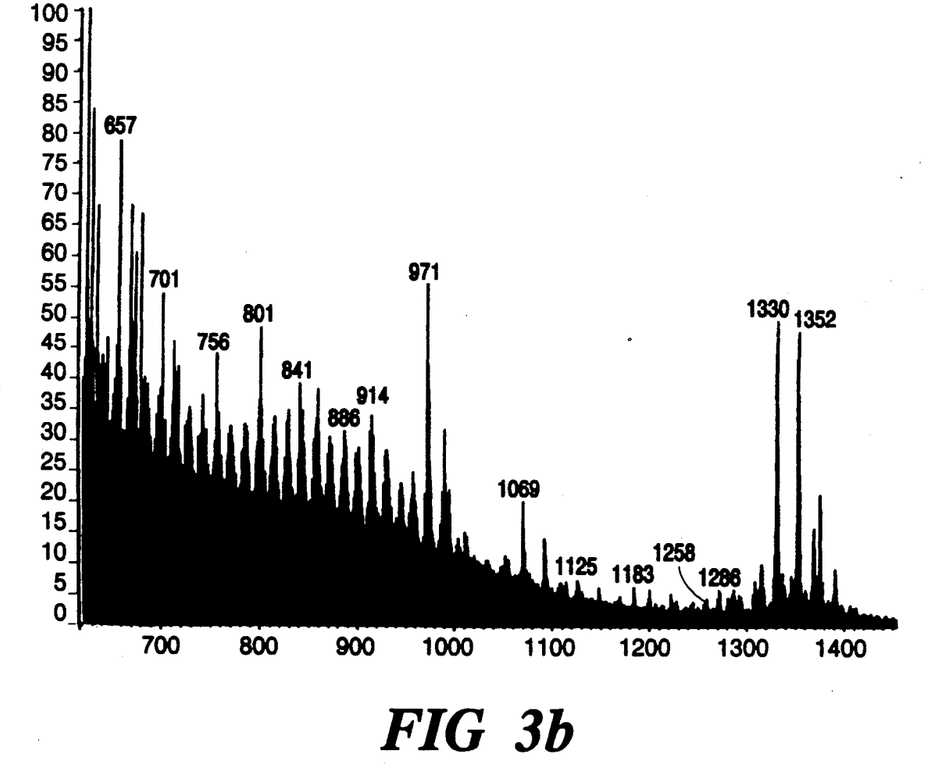
FIG. 3b is the positive ion flow-FAB mass spectrum of coenzyme $B_{12}$ extract.

FIGS. 3a and 3b show the positive ion flow-FAB mass spectrum of coenzyme $B_{12}$. These mass spectra were recorded with the device of the present invention. There was no $(M+H)^+$ ion at m/z 1580 present; however, a significant fragment ion at m/z 1330 is seen. This fragment arises from the loss of the 5'-deoxyadenosyl group from the pseudomolecular ion. An additional loss of the ribofuranyl group yields the ion at m/z 1069. The mass spectrum of the extracted material is again identical to that of the standard.

FIG. 3a is the positive ion flow-FAB mass spectrum of a standard solution of coenzyme $B_{12}$. This spectrum was obtained in the dip-and-suck method of flow-FAB, that is the capillary leading into the MS source was immersed in the solution, with the pressure difference between the atmosphere and the vacuum system of the mass spectrometer drawing sample continuously into the source. FIG. 3b shows the flow-FAB spectrum obtained for the same compound, this time extracted out of the agarose gel. This spectrum is identical to that of the standard. The differences of indicated mass are due to rounding in the centroiding routines of the mass spectrometer data system. It should be noted that these two spectra were obtained using the MCA mode with magnet scanning to enhance the sensitivity of the analysis.

Figure 4A:
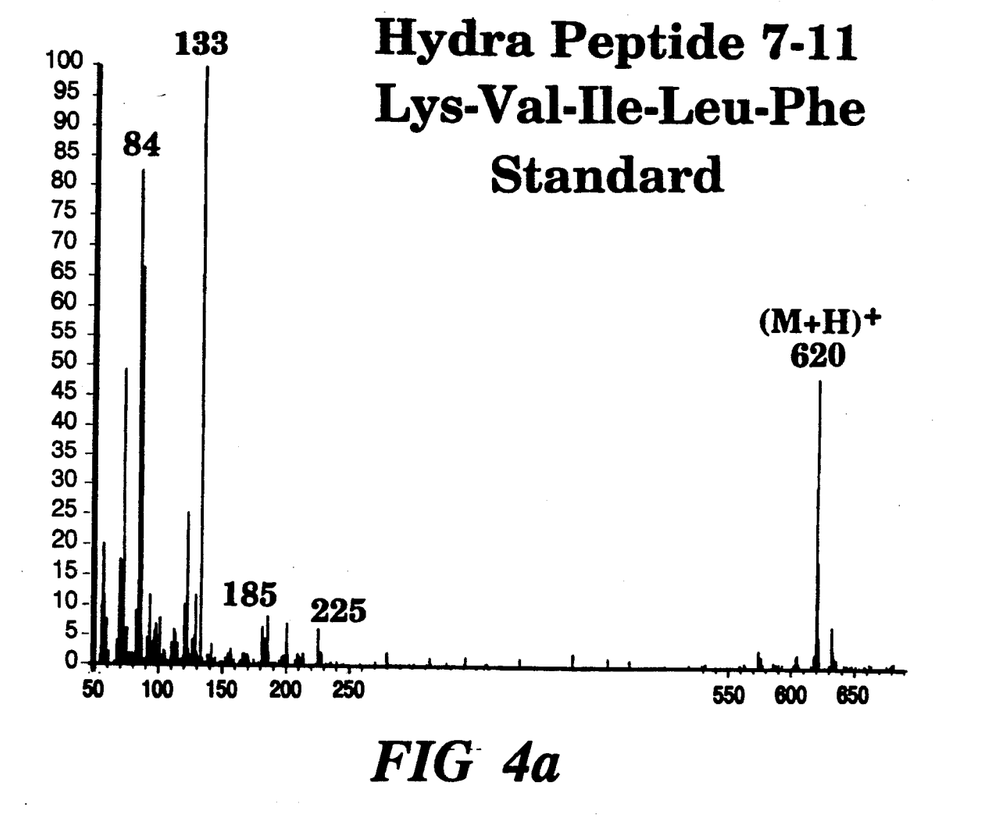
FIG. 4a is the mass spectrum of hydra peptide 7–11 Lys-Val-Ile-Leu-Phe standard.
Figure 4B:
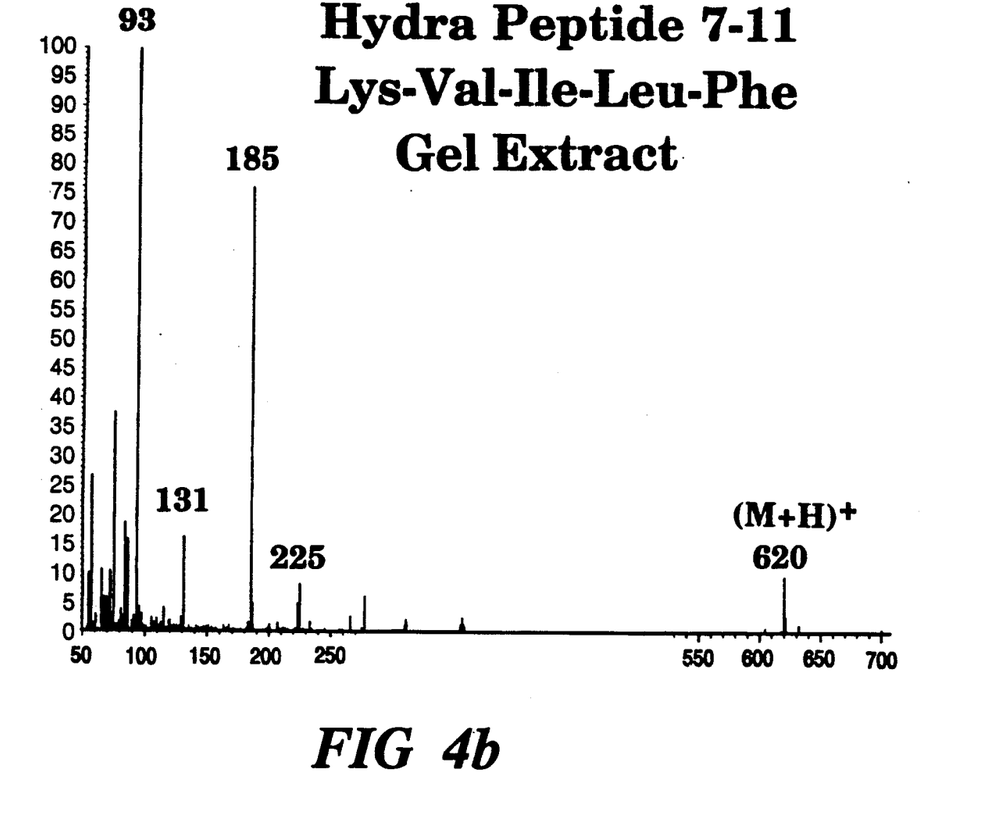
FIG. 4b is the mass spectrum of hydra peptide 7–11 Lys-Val-Ile-Leu-Phe extract.

FIG. 4a shows the positive ion flow-FAB mass spectrum of a pentapeptide, hydropeptide, solution standard. An abundant protonated molecular ion at m/z 620 is observed, as well as characteristic fragment ions. The ion at m/z 133 is due to the Cs+ from the primary ion beam. FIG. 4b shows the flow-FAB mass spectrum of the same sample extracted out of agarose gel.

Figure 5A:
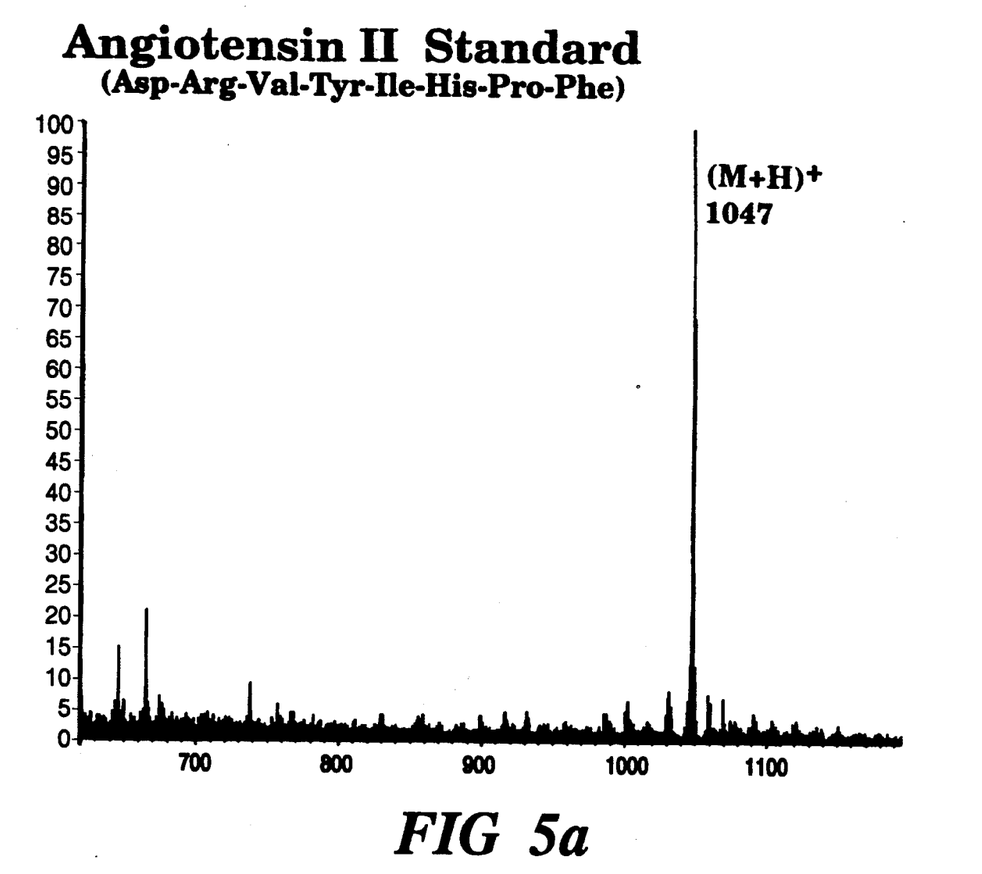
FIG. 5a is the mass spectrum of angiotensin II standard.
Figure 5B:
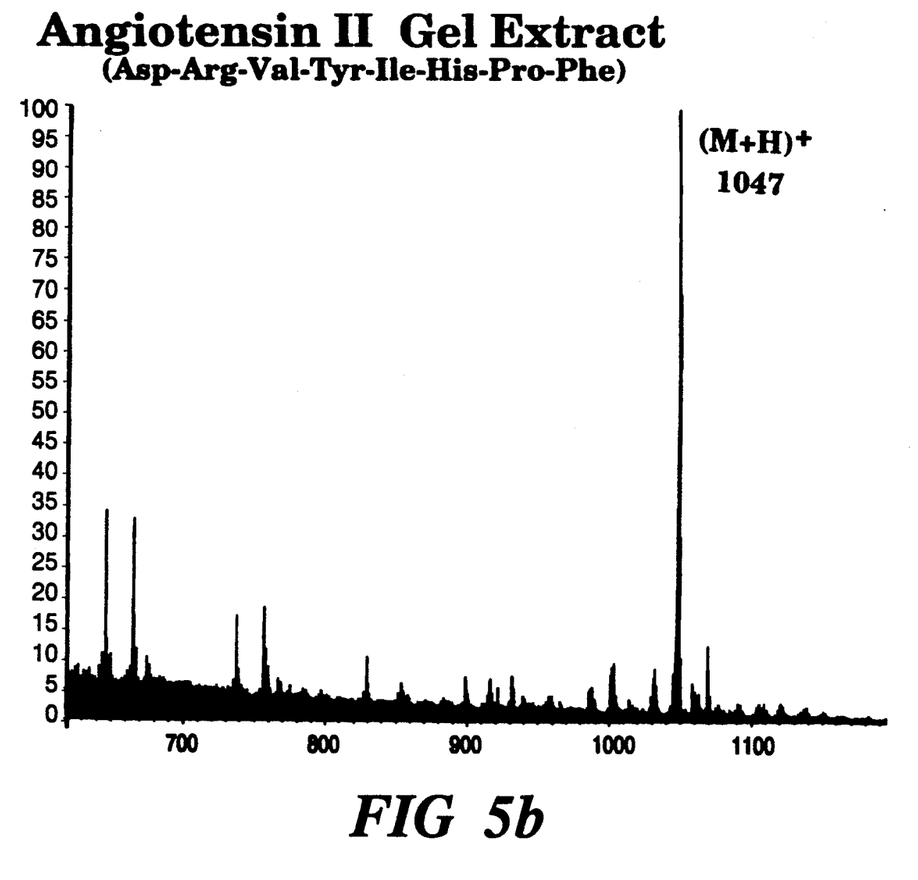
FIG. 5b is the mass spectrum of angiotensin II extract.

FIG. 5a shows the positive ion flow-FAB mass spectrum of an angiotensin II standard solution. An abundant $(M+H)^+$ ion at m/z 1047 is present, as well as characteristic fragment ions arising from this octapeptide. Sodium adduct ions, for instance m/z 1069, and glycerol cluster ions, m/z 645, 737, 829, and 917, also are present. FIG. 5b shows the flow-FAB mass spectrum of the same sample extracted from a solution obtained from the homogenized gel.

Significant sensitivity is obtained in using the present interface and useful mass spectrum can be generated for small amounts of sample, of the level generally present in actual electrophoretic separations. These amounts typically loaded onto the gels are in the high nanogram to low microgram range, that is, nano- or picomoles of material. The key to being able to obtain mass spectra of such small concentrations is due to the use of the preconcentration guard column. By concentrating the analyte from an aqueous solution on the head of the column, then back flushing the column with a stronger solvent such as methanol, the sample is analyzed as a plug of higher concentration.

The major obstacle preventing the interfacing of gel electrophoresis to mass spectrometry (and any other indirect detection scheme) has been the strong retention of the analyte molecules within the gel matrix itself. If the matrix can be disrupted in any way, the analyte is free to migrate out of the gel. Mechanical and ultrasonic disruption in conjunction with chemical disruption seems to be the key in forcing the release of the sample molecules.

Requirements for the solvent system are eased considerably because of the use of a mechanical disruption of the gel volume. However, the use of modified gels may ease the need for mechanical disruption, and may allow a more convenient means to decrease the volume sampled by the mass spectrometer. The special gels include a polyacrylamide gel that can be dissolved with periodic acid applied through the solvent capillary. Dissolution of this gel allows rapid migration of the analyte out of the gel matrix into the applied solvent. Extraction and transfer within a few seconds is the ultimate goal, as this will allow spatially resolved data to be recorded within a seasonable rime.

A low-melting agarose gel (35° C.) that can be disrupted not with a homogenizer, but rather with a resistively heated probe tip, also may be used. These gels may prove more amenable to sampling for mass spectrometry, but are not as widely used in normal biological procedures. The interface device described allows a more general application to gel materials in common use.

2. Other Applications

The present invention, when optimized in terms of filter configurations, flow volumes, and transfer times to the source of the mass spectrometer, allows direct examination by mass spectrometry of samples separated by planar gel electrophoresis. At least two major alternative applications can be accomplished with the present interface.

The first alternative application is the coupling of the sampling probe to more conventional, nondestructive means of sample visualization and detection, such as optical densitometry or fluorescence. Very sophisticated sample movement and optical detection devices are available, and the need to correlate mass spectral information with this independent information is evident. The mass spectrometer probe can be tied in with such an integrated imaging system. Optical scanning is followed by slave translation unit scanning with an automated rotor/stator or piezoelectric homogenizing probe. Alternatively, a large field-of-view documentation system with image analysis software can be used to drive an independent set of translation stages. Cross correlation of optical, UV/vis, fluorescence, radioimaging, mass spectrometric, and other data is ultimately possible.

The second alternative application is the coupling of the transfer capillary to an electrospray ionization source, which has been demonstrated to provide high quality mass spectra from large mass biomolecules of exactly the sort typically separated by PAGE or agarose gel electrophoresis. Since instruments such as the ion trap already have been shown to operate satisfactorily with electrospray ionization, a relatively small mass spectrometer may provide the most efficient way of coupling planar electrophoresis with mass spectrometry. The ability to produce multiply charged ions of biomolecules brought to the source in a solvent stream is completely compatible with the homogenization and transfer parameters already established.

It will be obvious to those skilled in the art that many variations may be made in the embodiment of the method and apparatus chosen for the purpose of illustrating the best mode of this interface without departing from the scope of the invention as defined by the following claims.

What is claimed is:

1. A method of introducing band samples from planar electrophoresis having at least one surface into a spectrometric device which comprises the steps of:
    a) providing a solvent if necessary;
    b) delivering said solvent to the surface of said electropherogram;
    c) disrupting said electropherogram so as to release a sample from within said electropherogram into said solvent; and
    d) transferring said sample containing solvent into a spectrometric device.

2. A method as defined in claim 1, wherein said sample is separated within an electropherogram.

3. A method as defined in claim 1, wherein said spectrometric device is a mass spectrometer.

4. A method as defined in claim 1, wherein said solvent is delivered to the surface of said sample at a specified rate.

5. A method as defined in claim 1, wherein said sample-containing solvent is transferred to said spectrometric device via a transfer capillary line.

6. A method of introducing a sample from a planar gel electropherogram into a spectrometric device, which comprises the steps of:
   a) providing a planar gel electropherogram having a surface containing sample bands to be analyzed;
   b) isolating the surface of a section of said electropherogram;
   c) providing a solvent and delivering said solvent to the initial surface of said electropherogram;
   d) disrupting said isolated surface thereby releasing a sample from within said electropherogram so that it can be taken up into said solvent; and
   e) transferring said sample containing solvent into said spectrometric device.

7. A method as defined in claim 6, Wherein said solvent is delivered to the surface of said electrophoresis at a specified rate.

8. A method as defined in claim 6, wherein said sample containing solvent is transferred to said mass spectrometer via a transfer capillary line.

9. A system for introducing sample to a spectrometric device comprising:
   a) a sample removal means comprising a solvent introduction means for introducing a solvent to the sample, a sample disruption means for disrupting the sample so as to release molecules of the sample into the solvent, and a sample withdrawal means for withdrawing said sample containing solvent from the sample; and
   b) an introduction means for transferring said sample containing solvent from said sample removal means and introducing said sample containing solvent into said spectrometric device.

10. The system as defined in claim 9, wherein said sample is a band from a planar gel electropherogram.

11. The system as defined in claim 10, wherein said gel is a low melting point gel.

12. The system as defined in claim 10, wherein said gel is soluble in said solvent.

13. The system as defined in claim 9, wherein said spectrometric device is a mass spectrometer.

14. The system as defined in claim 9, wherein said solvent introduction means, said sample disruption means, and said sample withdrawal means are contained on a probe means.

15. The system as defined in claim 14 wherein said sample disruption means is a piezoelectric ultrasonic device.

16. The system as defined in claim 14, wherein said disruption means is a heated probe means.

17. The system as defined in claim 14, wherein said disruption means is a rotor/stator homogenizer.

18. The system as defined in claim 14, wherein said disruption means is a laser.

19. The system as defined in claim 9, wherein said sample introduction means comprises a transfer capillary and a pump.

20. The system as defined in claim 19, wherein said sample introduction means further comprises a filtration column.

21. The system as defined in claim 20, wherein said filtration column comprises a means of sample concentration.

22. The system as defined in claim 20 further comprising a valve means, said valve means being selectively operable in two positions, said first position allowing said sample to be removed from said gel electrophoresis and introduced into said guard column, and said second position allowing said sample to be removed from said guard column and introduced into said mass spectrometer.

23. A system for introducing a sample taken from a planar electropherogram into a mass spectrometer comprising:
   a) means for providing a solvent;
   b) means for delivering said solvent to the surface of said planar electrophoresis;
   c) means for disrupting the surface of said planar electrophoresis and mixing said solvent with said disrupted surface of said planar electrophoresis;
   d) means for removing a portion of said mixture of said solvent and said disrupted surface of said planar electrophoresis; and
   e) means for introducing said sample to said mass spectrometer.

24. The system as defined and claim 23, further comprising a filtration column means.

25. The system as defined in claim 24, wherein said filtration column comprises a means of sample concentration.

26. The system as defined in claim 24, further comprising a valve means, said valve means being selectively operable in two positions, said first position allowing said sample to be removed from said planar electrophoresis and introduced into said filtration column means, and said second position allowing said sample to be removed from said filtration column means and introduced into said mass spectrometer.

27. The system as defined in claim 23, wherein said means for disrupting the surface of said planar electrophoresis comprises a means of heating the electropherogram surface.

* * * * *